(12) United States Patent
Emig et al.

(10) Patent No.: US 7,713,536 B2
(45) Date of Patent: *May 11, 2010

(54) PREPARATION, IN PARTICULAR COSMETIC PREPARATION, AND THE PRODUCTION AND USE THEREOF

(75) Inventors: Susanne Emig, Nuremberg (DE); Sonja Engelhardt, Eckental-Oberschoellenbach (DE); Sabine Lober, Nuremberg (DE)

(73) Assignee: Schwan-STABILO Cosmetics GmbH & Co. KG, Heroldsberg (DE)

( * ) Notice: Subject to any disclaimer, the term of this patent is extended or adjusted under 35 U.S.C. 154(b) by 401 days.

This patent is subject to a terminal disclaimer.

(21) Appl. No.: 11/189,255

(22) Filed: Jul. 26, 2005

(65) Prior Publication Data

US 2006/0051383 A1    Mar. 9, 2006

(30) Foreign Application Priority Data

Sep. 6, 2004    (DE) ............ 20 2004 014 004 U
May 3, 2005    (DE) ............ 10 2005 020 583

(51) Int. Cl.
*A61K 8/02* (2006.01)
*A61Q 5/12* (2006.01)

(52) U.S. Cl. .................. 424/401; 424/70.12
(58) Field of Classification Search ............. 424/401, 424/70.12
See application file for complete search history.

(56) References Cited

U.S. PATENT DOCUMENTS

| | | | |
|---|---|---|---|
| 4,230,655 A | 10/1980 | Kruckel et al. | |
| 4,486,110 A | 12/1984 | Kruckei et al. | |
| 5,635,165 A | 6/1997 | Panitch | |
| 5,763,497 A | 6/1998 | Ikeda et al. | |
| 6,171,580 B1 | 1/2001 | Katsuyama et al. | |
| 6,183,761 B1 | 2/2001 | Bissett et al. | |
| 6,238,117 B1 | 5/2001 | Griebel et al. | |
| 6,251,423 B1 * | 6/2001 | Bradford | 424/443 |
| 6,309,128 B1 | 10/2001 | Griebel et al. | |
| 6,607,717 B1 | 8/2003 | Johnson et al. | |
| 6,958,155 B2 * | 10/2005 | Lu et al. | 424/401 |
| 2002/0034548 A1 * | 3/2002 | Parr et al. | 424/489 |
| 2002/0192172 A1 | 12/2002 | Chopra et al. | |
| 2003/0133895 A1 | 7/2003 | China et al. | |
| 2003/0185772 A1 | 10/2003 | Kouzuki et al. | |
| 2003/0206883 A1 | 11/2003 | Yang | |
| 2004/0120913 A1 | 6/2004 | Shah et al. | |
| 2004/0258638 A1 | 12/2004 | Wendel et al. | |
| 2005/0008596 A1 | 1/2005 | Biatry et al. | |
| 2005/0249689 A1 | 11/2005 | Kuo et al. | |
| 2008/0051470 A1 | 2/2008 | Issberner et al. | |
| 2008/0249192 A1 | 10/2008 | Goget et al. | |

FOREIGN PATENT DOCUMENTS

| | | |
|---|---|---|
| DE | 2718957 | 11/1978 |
| DE | 2759610 | 11/1978 |
| DE | 2759856 | 11/1978 |
| DE | 3028231 | 3/1982 |
| DE | 4005894 | 12/1991 |
| DE | 696 00 112 | 3/1998 |
| DE | 696 14 578 | 6/2002 |
| DE | 101 57 542 | 6/2003 |
| DE | 10234885 | 2/2004 |
| DE | 10241074 | 3/2004 |
| DE | 69914726 | 12/2004 |
| DE | 102004017222 | 10/2005 |
| DE | 601 12 916 | 2/2006 |
| DE | 10234884 | 11/2009 |
| EP | 0179416 | 4/1986 |
| EP | 0 756 864 | 8/2004 |
| EP | 1 543 811 | 6/2005 |
| FR | 2822058 A1 * | 9/2002 |
| FR | 2835432 A1 * | 8/2003 |
| GB | 2081579 | 2/1982 |
| WO | 96/18374 | 6/1996 |
| WO | 01/91704 | 12/2001 |

OTHER PUBLICATIONS

ABIL EM 90.

* cited by examiner

*Primary Examiner*—Sreeni Padmanabhan
*Assistant Examiner*—Samira Jean-Louis
(74) *Attorney, Agent, or Firm*—Bachman & LaPointe, P.C.

(57) ABSTRACT

A preparation, in particular a cosmetic preparation, in the form of a workable paste which is present in the form of a W/O emulsion and which is suitable for cosmetic uses, in particular in the area of decorative cosmetics for coloring and improving the skin, the lips and the eyelids. It is also suitable as a fixing for lipstick, as lip care, as a skin care foundation or as a sun protection agent. It is preferably in the form of a water-in-silicone emulsion. It contains a wax, a suitable emulsifier, a volatile silicone oil, a moistening agent, a solid phase and water. In addition it may also contain the additives and adjuvant substances which are approved and usual in cosmetics. Processes for the production of the preparation are also described.

21 Claims, No Drawings

PREPARATION, IN PARTICULAR COSMETIC PREPARATION, AND THE PRODUCTION AND USE THEREOF

BACKGROUND OF THE INVENTION

The invention concerns a preparation, in particular a cosmetic preparation, which is present as a W/O emulsion in the form of a workable paste and is suitable for cosmetic uses, in particular in the region of decorative cosmetics, for coloring and improving the appearance of the skin, lips and eyelids. By way of example mention may be made here of lip rouge, blusher. makeup or eyeshadow. It can also be used as a fixing agent for the lips, as a skin care foundation or as a sun protection agent. That preparation, in particular a cosmetic preparation, occurs preferably in the form of a water-in-silicone emulsion.

Preparations of the specified kind usually contain lipid-like substances such as for example fats, oils, oil-soluble vegetable extracts and medium to long-chain fatty acids and waxes, as well as volatile or non-volatile silicone oils and silicone copolymers such as silicone resins and silicone gels. Silicone oils that may be mentioned are volatile cyclic silicone oils such as octamethylcyclotetrasiloxane, decamethylcyclopentasiloxane, dodecamethylcyclohexasiloxane, and linear short-chain siloxanes such as hexamethyldisiloxane or octamethyltrisiloxane, while non-volatile silicone oils that may be mentioned include the so-called dimethylpolysiloxanes in a wide range of different chain lengths and different viscosities and arylated silicone oils such as for example phenyl dimethicones, phenyl trimethicones, diphenyl dimethicones and others.

In addition they may contain a solid phase comprising finely divided fillers and coloring agents. Sun protection agents may use particularly finely divided pigments, so-called nanopigments, of an average particle size of between 5 and 50 nm, which act transparently on the skin and no longer color it. Silicon dioxide, titanium dioxide, cerium oxide, aluminum oxide, zirconium oxide and zinc oxide may be mentioned here by way of example.

A disadvantage with such preparations is that they can be easily transferred from the skin or the lips to which they are regularly applied on to other surfaces, for example cups, glasses, textiles or other areas of the skin. That can leave behind traces in the form of a colored mark or a greasy film. Such products therefore have insufficient adhesion to the underlying surface to which they are applied, with the result that lipstick and blusher, makeup, eyeshadow and also sun protection agents have to be regularly re-applied. As oily constituents generally spread very well on the skin, the pigments move from the original place of application together with small amounts from the oily phase into the fine wrinkles and creases in the skin in the immediate surroundings, which often has a very disturbing and adverse effect on the overall visual impression.

In the past the attempt was made to counteract that in relation to lipsticks and lip rouge by the use of so-called 'bromo acids', dyestuffs which substantively gather on the skin. As however, due to differing pH-values of the skin, those dyestuffs gave individually different and unpredictable shades and in addition the coloring effects often persisted for days, that route was immediately abandoned again because the lady consumers only inadequately accepted products of that nature.

After silicone oils and silicone resins had found their way into cosmetics, the attempt was made to improve the adhesion to the skin and thus the durability of decorative preparations thereby. Thus from about 1977 eyeshadow pencils and lipsticks have been known in the form of leads which were cast into sharpenable casings which in the lipid phase contained inter alia a mixture of phenyl trimethicone (a non-volatile silicone oil) and cyclomethicone (a volatile silicone oil). They were then followed by similar preparations which contained cyclomethicone as the sole silicone component. Although they had an apparently firm structure, those pencil materials could be applied to the skin in a soft and malleable fashion, similarly to a pasty material. After evaporation of the volatile silicone, there was left behind on the skin a soft elastic film which had very good adhesion and which moved only to a minimum extent into the area surrounding the original location at which it was applied. The principle of combining two silicone oils, applied to pasty preparations, is also to be found again for example in EP 0 756 864.

In spite of the highly positive effects in terms of adhesion and durability, such preparations of the kind known hitherto which contain silicone oil can give rise to detrimental effects on the part of sensitive users if they are used in the immediate proximity of the eye. More specifically, if even minimum amounts of silicone oils, in particular non-volatile silicone oils or other silicone polymers from the products in pencil form which are known from the state of the art pass into the eye or the conjunctiva sac, they can lead to an oily film on the lens and unpleasant irritation, referred to as the 'wind burn effect'.

DETAILED DESCRIPTION

Surprisingly it has now been found that a preparation and in particular a cosmetic preparation in the form of a water-in-silicone emulsion does not exhibit the above-indicated disadvantages if, besides at least one volatile silicone oil and water as volatile components it contains no further oil components—at best it is still possible to use a low-viscosity non-volatile silicone oil in quite low amounts below 5% by weight, which delays the drying time of the preparation and at the same time acts as an antifoam agent and emulsion aid.

Therefore the object of the invention was to provide a preparation, in particular a cosmetic preparation, which does not suffer from the known disadvantages of the products of the state of the art and which is present in emulsion form as a workable paste, preferably in the form of a water-in-silicone emulsion. The invention seeks to provide that that preparation is suitable for cosmetic uses, in particular in the area of decorative cosmetics, for coloring and improving the appearance of the skin, the lips and the eyelids, such as for example in the form of lip rouge and blusher, makeup, concealer, eyeshadow, a fixing agent for fixing lipstick or lip rouge, as a skin care foundation or as a sun protection agent. The invention further seeks to provide that that preparation; in particular a cosmetic preparation, after drying, does not move either on the skin or the lips, in addition it is wipe-resistant and it is not transferred on to other surfaces such as for example cups, glasses, textiles or other areas of the skin—therefore it is to be transfer-resistant. On the other hand however, by virtue of its pronounced structural viscosity, that preparation and in particular the cosmetic preparation are to be capable of being applied easily and workably and in differing layer thicknesses in order to make it possible, after application, to achieve smooth and gentle transitions to the untreated skin; in addition the preparation is not to become tight on the skin or the lips and it is not to dry them out. In addition the invention seeks to provide that the preparation is stable in respect of storage at the different temperatures of the different climatic zones and it is stable in respect of storage at least within the limits the statutory requirements in that respect. It is not to exhibit any syneresis effects even after a prolonged storage time.

The complex viscosity of this preparation is in the region of between 800 and 6000 Pas and the neutral viscosity is between 200,000 and 1,200,000 Pas (shearing rate at neutral viscosity 0.00005 s$^{-1}$; temperature 298.15 K; measuring system plate/plate, plates both sand-blasted, plate diameter 25 mm, gap width 1000 µm; measuring device MCR-301, Anton Paar; software Rheoplus/32 V6.23).

The viscosity is also to change only immaterially even during a prolonged storage time. Preferably that preparation has structurally viscous properties, which facilitates application, but the stability of the formulation in the container and in the rest condition counteracts settlement of specifically heavier ingredients.

A further object of the invention was to provide a preparation and in particular a cosmetic preparation containing ingredients which can be derived exclusively from vegetables and/or which are mineral and/or synthetic, but which otherwise is completely free of substances which derive from animals.

In order very substantially to minimise mutual interactions between the ingredients used, the basis of this preparation—without the solid phase which is possibly used—should in addition be composed of as small a number of substances as possible.

This object is attained in that a preparation, in particular a cosmetic preparation, in the form of a water-in-silicone emulsion is provided, which as sole fluid lipid components contains volatile silicone oils, for example cyclomethicones such as hexamethylcyclotrisiloxane, octamethyltetrasiloxane, decamethylcyclopentasiloxane, dodecamethylcyclohexasiloxane or short-chain dimethicones such as hexamethylsiloxane, octamethyltrisiloxane, decamethyltetrasiloxane, dodecamethylpentasiloxane or mixtures thereof, wherein the amount thereof used is between 5 and 65% by weight with respect to the total weight of the preparation, preferably between 15 and 45% by weight, and optionally non-volatile silicone oils in a small amount as an antifoam agent and emulsifying aid, in amounts markedly below 5% by weight. In addition at least one wax component is used having a dropping point of between 50 and 200° C., preferably between 60 and 150° C., quite particularly preferably between 75 and 120° C. That wax component contains at least one alcohol residue of a chain length of between $C_2$ and $C_{60}$ and a carboxylic acid residue with a chain length of between $C_4$ and $C_{60}$. Both the alcohol residue and also the carboxylic acid residue can have a saturated or a singly or multiply unsaturated, straight-chain or branched chain hydrocarbon component and optionally also still further substituents in the form of functional groups such as hydroxyl, carboxyl, amino, acid amide, and ester groups and the like. Preferably esters of pentaerythritol such as for example pentaerythrityl tetramyristate, tristearate, tetrastearate, triisostearate, tetraisostearate, tri-(12-hydroxy)-stearate, tetra-(12-hydroxy)-stearate, tribehenate, tetrabehenate, tetra-(ethylhexyl-dodecanoate), trierucate, tetraerucate, tetramelissinate and the like. It is also possible to use behenylbehenate, behenylmelissinate or isostearyl-ethylhexyldodecanoate. It is also possible to use a mixture of candellila wax and carnauba wax. In principle it is also possible to use mixtures of the above-mentioned wax esters; on the premise that unwanted interactions between the individual components are to be minimised, preferably however only one of the above-mentioned wax components is used. Those wax components are used in amounts which are required to achieve the desired neutral viscosity, in accordance with the desired purpose of use. In that respect the amounts used are in a quantitative range of between 0.5 and 20% by weight, preferably in a range of between 2 and 12% by weight. Surprisingly it was found in that respect that the esters deriving from pentaerythritol—no doubt because of the three-dimensional spatial structure deriving from the tetrahedron model—are very well suited to excellently well gelling volatile silicone oils such as for example cyclomethicones or short-chain dimethylpolysiloxanes and in that way providing thixotropic structures which facilitate application of the preparation according to the invention.

To form the W/O emulsions according to the invention—in the specific case water-in-silicone emulsions—at least one emulsifier, preferably a non-ionogenic emulsifier, is used, selected for example from sorbitan sesquioleate, sorbitan laurate, polyglyceryl-4 isostearate, PEG-5 soya sterol, soya sterol, polyglyceryl-2-PEG-4 isostearate, polyglyceryl-2 sesquiisostearate or cetyl PEG/PPG dimethicone, such as for example cetyl PEG/PPG-10/1 dimethicone. In that respect experience has shown that soya sterols are preferably suitable as auxiliary emulsifiers. It will be appreciated that basically it is also possible to use mixtures of the above-mentioned W/O emulsifiers—on the premise that undesired interactions between the individual components are to be minimised however preferably only one of the above-mentioned W/O emulsifiers is used for the production of water-in-silicone emulsion according to the invention. Basically however phosphate esters are also suitable as W/O emulsifiers for production of the preparation according to the invention such as for example trioleyl phosphate, trioleth-8 phosphate or trilaureth-4 phosphate.

The amounts of W/O emulsifiers required are in the range of between 0.5 and 10% by weight, preferably between 1.5 and 6% by weight. To stabilise the water-in-silicone emulsions, it is possible to add to the water phase optionally inorganic salts which are easily soluble in water or salts (virtually insoluble in water) of fatty acids such as for example magnesium sulfate, sodium sulfate, sodium chloride, potassium chloride, magnesium stearate or magnesium myristate. The two last-mentioned components are to be carefully dispersed in the water phase prior to emulsion formation; preferably however they can also be added to the solid phase. The above-mentioned salts are used in amounts of between 0.05 and 3% by weight, but preferably between 0.3 and 2% by weight, in the water phase.

In addition it is also possible to add to the water phase at least one agent for keeping the preparation moist such as for example propylene glycol, dipropylene glycol, tripropylene glycol, butylene glycol, glycerine, diglycerine, triglycerine, sorbitol, mannitol, xylitol, glucose, fructose, sucrose, carbamide (urea), lactic acid, citric acid, pyrrolidone carboxylic acid (PCA) or the salts of said acids or mixtures of said substances. Preferably in that respect the sodium salts which are easily soluble in water are used. The amounts used are between 0.1 and 5% by weight, preferably between 1 and 3% by weight.

For stabilisation over a relatively wide temperature range silica (amorphous silicic acid), bentonite, hectorite, montmorillonite and the like is used. In addition it is also possible to use additives which are conventional in cosmetics such as preserving agents, antioxidants, perfumes, vitamins, sun protection filters and the like.

The above-mentioned solid phase can comprise fillers such as for example talcum, kaolin, starch and modified starch, polytetrafluoroethylene powder (Teflon), nylon powder, boronitride, insoluble metal salts such as Mg stearate, Ca stearate, Sr stearate, Zn stearate and inorganic or organic pigments. The following may be mentioned by way of example of the latter: titanium dioxide, zinc oxide, iron oxides, chromium oxide, chromium hydroxide, ultramarine, Berlin blue (ferric blue), mica, pearl sheen agents such as for example mica coated with titanium dioxide, colored mica coated with titanium dioxide and metal oxides, bismuth oxide chloride, coated bismuth oxide chloride, metal powder in flake form of aluminum, brass, bronze, copper, silver, gold and laking means of organic coloring agents with aluminum, barium, calcium or strontium. That list is only given by way of example and is not definitive—it is to be noted in that respect that the coloring agents used and in particular the laking means of organic coloring agents do not bleed out in conjunction with water. Those additions are implemented with the proviso that they are also approved by the respective national or regional cosmetic legislation. Also the amounts used are within the limits of the highest amounts permitted by the respective cosmetic legislation. In that respect, the quantitative proportions of solids and in particular the pigments, insofar as no statutory regulations prohibit this, are in a range of between 0 and 40% by weight and preferably in a range of between 5 and 30% by weight and quite particularly preferably in a range of between 8 and 20% by weight.

It was surprisingly found that the preparations according to the invention based on pearlescent pigments and metal powders in flake form are distinguished by an unusually intensive sheen—evidently the nature of that water-in-silicone emulsion causes a particular orientation of those pigment particles—perhaps caused by the controlled evaporation of the volatile constituents silicone oil and water and thus perhaps the possibility of being oriented at active charge centers of the skin.

Because of their excellent durability and coverage in conjunction with the extremely good application properties, the above-mentioned preparations according to the invention can certainly also be used as camouflage for concealing age spots or rosacea, concealer and the like, and also sun protection products with different sun protection factors (SPF), as far as so-called sun blocks, using very finely divided nanopigments or brightly colored, more highly pigmented sun blocks, which are popular with surfers and windsurfers as body paint. The specified nanopigments are preferably of a particle size of between 5 and 50 nm and can be selected from titanium dioxide, zinc oxide, cerium oxide or aluminum oxide. They are preferably used in amounts of between 2 and 20% by weight, particularly preferably in amounts of between 5 and 10% by weight.

The preparation can also be produced without the addition of coloring agents and may optionally contain so-called cosmetic active substances. It is then used as a fixing agent which is applied over a lipstick or lip rouge. If that uncolored preparation contains light protection filter, it can be used as lip protection and lip care. As is known in contrast to the skin of the body the skin of the lips does not contain any pigmentation. Suitable oil-soluble light filter substances which afford good protection in the TV-A and UV-B range are known in adequate numbers to the man skilled in the relevant art and are regulated by the respective national and regional legislation for example in the EU, in Japan and in the USA—in Germany for example by Appendix 7 to Regulation 3b of the Cosmetics Regulations and they are therefore not to be comprehensively listed here. Therefore mention will only be made by way of example of isoamyl p-methoxycinnamate as a UV-B filter and 4-methylbenzylidene camphor as a UV-A filter.

The preparation according to the invention is in the form of a soft workable paste which can be easily and uniformly applied and distributed. By virtue of its water content in the inner (disperse phase) upon application to the skin, in conjunction with the volatile silicone oils, it produces a pleasantly cooling effect. It can be removed again from the skin in a manner known to the users—by suitable makeup removal agents or cloths or by washing with fine soap or suitable mild tenside preparations. It can be filled in known manner into suitable vessels such as bottles, possibly with a spatula, pots or tubes, and can be removed again therefrom by the user. However, because of the improved hygiene conditions involved therewith, it can also be introduced into suitable applicator devices, so-called dispenser mechanisms, and applied therefrom. Applicator devices as are known for example from U.S. Pat. No. 6,238,117 or U.S. Pat. No. 6,309,128 present themselves for the application of small amounts as are required for example for application in the region of lips or eyes, as those devices permit very nice fine metering.

The preparation according to the invention, in particular the cosmetic preparation, will now be described in detail by means of the Examples hereinafter, which however do not definitively describe the invention. In this respect all amounts are stated in percent by weight (% by weight) with respect to the total weight of the preparation, the raw materials are identified by the INCI names which are generally known to the man skilled in the relevant art:

Example 1

Cream Eyeshadow, Cooling (Non-Transfer)

| Decamethylcyclopentasiloxane | 26.300 |
| Pentaerythrityl tetrabehenate | 5.900 |
| Cetyl PEG/PPG-10/1 dimethicone | 3.800 |
| Glycerine | 3.750 |
| Sodium chloride | 0.800 |
| Methylparabene | 0.200 |
| Propylparabene | 0.100 |
| Phenoxyethanol | 0.500 |
| Ascorbyl palmitate | 0.100 |
| Tocopherol | 0.350 |
| Fragrance | 0.300 |
| Titanated mica (C.I. No 77019, 77891) | 9.500 |
| Titanium dioxide (C.I. No 77891) | 3.500 |
| Red iron oxide (C.I. No 77491) | 1.000 |
| Yellow iron oxide (C.I. No 77492) | 0.600 |
| Black iron oxide (C.I. No 77499) | 0.400 |
| Aqua | 42.900 |

Production is effected by a procedure whereby the pigments are put with the silicone oil very intensively in a suitable homogenising machine with an anchor-type agitator and gear ring homogeniser and intensively dispersed by means of the homogeniser. Thereafter the tetrabehenyl tetrabehenate is added together with the emulsifier and melted at about 70-80° C. The parabenes, phenoxyethanol, ascorbyl palmitate and tocopherol are now added to the melt. The glycerine and sodium chloride were dissolved in water in a separate vessel and then the water phase was heated to about 70° C. The water phase is now sucked into the homogenisation machine with strong agitation. After the end of the addition the batch is intensively homogenised and then cooled down with strong agitation. At about 45° C. it is briefly homogenised once again then further cooled with agitation to about 38° C. At that temperature fragrance (the perfume mixture) is added and homogenisation is briefly effected once again. The substance is now deaerated by the application of maximum vacuum and further agitated until a temperature of about 25° C. is reached. It is then discharged and filled into suitable storage containers. That affords a preparation in the form of a light-brown, strongly shiny, water-resistant, workable paste with a neutral viscosity of 853,000 Pas.

Example 2

Cream Eyeshadow, Cooling (Non-Transfer)

| | |
|---|---|
| Hexamethylsiloxane | 25.500 |
| Pentaerythrityltetrabehenate | 4.600 |
| Sorbitan sesquioleate | 3.800 |
| Butane-1,3-diol | 3.500 |
| Titanated mica (C.I. 77019, 77891) | 15.500 |
| Ultramarine blue (C.I. 77013) | 5.800 |
| Chromium hydroxide green (C.I. 77289) | 1.200 |
| Black iron oxide (C.I. 77499) | 0.800 |
| Tocopherol | 0.500 |
| Fragrance | 0.150 |
| Methylparabene | 0.200 |
| Propylparabene | 0.150 |
| Ascorbyl palmitate | 0.100 |
| Magnesium sulfate | 0.700 |
| Aqua | 37.500 |

Production is effected similarly to the operating procedure described in Example 1. It will be appreciated that care is to be taken to ensure that the pearl pigment, as is familiar to the man skilled in the relevant art, is not exposed to severe shearing forces for too long. The result obtained is a water-resistant, workable paste which is blue with a green cast, with an excellent cooling effect and which can be well applied to the eyelids. The above preparation has a neutral viscosity of 451,000 Pas. Experience has shown that somewhat different viscosity values can occur when using other pigment combinations in different amounts.

Example 3

Lip Rouge (Cooling, Water-Resistant)

| | |
|---|---|
| Hexamethyldisiloxane | 23.500 |
| Pentaerythrityl tetraerucate | 5.200 |
| Trioleyl phosphate | 4.100 |
| Butylene-1,3-glycol | 3.500 |
| Magnesium sulfate | 1.000 |
| Methylparabene | 0.200 |
| Propylparabene | 0.100 |
| Phenoxyethanol | 0.500 |
| Ascorbyl palmitate | 0.100 |
| Tocopherol | 0.300 |
| Fragrance | 0.150 |
| Titanated mica (C.I. No 77019, 77891) | 11.500 |
| Titanium dioxide (C.I. No 77891) | 2.800 |
| Red iron oxide (C.I. No 77491) | 2.200 |
| FD&C Yellow No 5 Al-Lake (C.I. 19140:1) | 0.800 |
| FD&C Red No 3 Al-Lake (C.I. 45430:1) | 0.700 |
| Aqua | 39.350 |

Production is effected similarly to the above-described mode of operation. The result obtained is a powerfully red preparation with a strong sheen, in the form of a water-resistant, workable paste with a neutral viscosity of 491,000 Pas, which is particularly well suited for the automatic applicator devices described hereinbefore.

Example 4

Lip Rouge with Sun Protection Filter (Cooling, Water-Resistant)

| | |
|---|---|
| Decamethylcyclopentasiloxane | 22.500 |
| Dodecamethylcyclohexasiloxane | 3.500 |
| Pentaerythrityl tetraerucate | 4.800 |
| Polyglyceryl-2-PEG-4 isostearate | 3.800 |
| Glycerine | 3.700 |
| Sodium chloride | 0.600 |
| Methylparabene | 0.200 |
| Propylparabene | 0.150 |
| Phenoxyethanol | 0.600 |
| Ascorbyl palmitate | 0.100 |
| Tocopherol | 0.250 |
| Fragrance | 0.150 |
| Titanated mica (C.I. 77019, 77891) | 7.000 |
| Titanium dioxide nanopigment (C.I. 77891) | 6.000 |
| Isoamyl p-methoxycinnamate | 1.500 |
| 4-Methylbenzylidene camphor | 2.000 |
| Red iron oxide (C.I. 77491) | 2.000 |
| Titanium dioxide (C.I. 77891) | 2.500 |
| D&C Red No 6, Ba-Lake (C.I. 15850:2) | 3.500 |
| Aqua | 35.150 |

Production is effected similarly to the above-described Examples. The result obtained is a workable paste which is colored with a powerful red and with a fine pearl sheen, for protecting the lips from strong sunshine. It has a neutral viscosity in the region of 386,000 Pas.

Example 5

Sunblock for Surfers (Water Resistant)

| | |
|---|---|
| Hexamethyldisiloxane | 24.000 |
| Phenyltrimethicone | 0.800 |
| Pentaerythrityl tetrabehenate | 4.800 |
| Pentaerythrityl tetra-(12-hydroxy)-stearate | 1.000 |
| Sorbitan sesquioleate | 4.200 |
| Iron oxide red (C.I. No 77491) | 3.200 |
| Iron oxide yellow (C.I. No 77492) | 1.800 |
| Propane-1,2-diol | 3.800 |
| Titanium dioxide (nanopigment) | 10.000 |
| Iron oxides (red and yellow) | 5.000 |
| Polyester-3, orange 5 | 7.500 |
| Isoamyl p-methoxycinnamate | 3.500 |
| 4-Methylbenzylidene camphor | 2.500 |
| Tocopherol | 0.600 |
| Fragrance | 0.200 |
| Methylparabene | 0.200 |
| Propylparabene | 0.150 |
| Ascorbyl palmitate | 0.100 |
| Sodium chloride | 0.600 |
| Aqua | 31.050 |

Production is effected similarly to the above-described mode of operation. The result obtained is a preparation in the form of a water-resistant, workable paste with an intensively orange-yellow coloring and a neutral viscosity of 780,000 Pas.

Example 6

Agent for Fixing Lipstick and Lip Rouge
(Wipe-Resistant)

| | |
|---|---|
| Decamethylcyclopentasiloxane | 32.500 |
| Phenyltrimethicone | 0.500 |
| Pentaerythrityl tribehenate | 6.200 |
| Sorbitan sesquioleate | 4.750 |
| Tocopherol | 0.300 |
| Diglycerine | 3.000 |
| Magnesium stearate | 2.800 |
| Fragrance | 0.200 |
| Methylparabene | 0.200 |
| Propylbarabene | 0.150 |
| Ascorbyl palmitate | 0.100 |
| Magnesium sulfate | 0.600 |
| Aqua | 48.700 |

Production is effected similarly to the foregoing Examples—here the magnesium stearate is dispersed intensively in silicone oil—otherwise the procedure is as described in Example 1. The result obtained is a white creamy preparation which leaves behind on the lips a transparent film with a pleasant cooling effect. The preparation has a neutral viscosity of 685,000 Pas.

The invention claimed is:

1. A water-in-silicone emulsion cosmetic preparation consisting of:
   (1) at least one pentaerythritol ester as a wax in an amount between 0.5 and 20% by weight;
   (2) at least one volatile silicone oil;
   (3) at least one non-ionogenic emulsifier;
   (4) at least one moistening agent present in the water phase in an amount between 0.1 and 5% by weight;
   (5) at least one solid phase;
   (6) a stabilization agent in the water phase in an amount between 0.05 and 3% by weight;
   (7) additives conventional in cosmetics;
   (8) and water;
wherein the preparation is a water-in-silicone emulsion, is in the form of a soft paste, and consists exclusively of ingredients which are derived from plants and/or which are minerals and/or synthetic and is completely free from substances derived from animals.

2. A preparation as set forth in claim 1, wherein the ester of pentaerythritol is selected from the group consisting of pentaerythrityl tetramyristate, tristearate, tetrastearate, triisostearate, tetraisostearate, tribehenate, tetrabehenate, tetra-(ethylhexyl-dodecanoate), tri-(12-hydroxy)-stearate, tetra-(12-hydroxy)-stearate, trierucate, tetraerucate, tetramelissinate and mixtures thereof.

3. A preparation as set forth in claim 1, wherein the wax is present in a range of between 2 and 12% by weight.

4. A preparation as set forth in claim 1, wherein the volatile silicone oil is selected from the group consisting of hexamethylcyclotrisiloxane, octamethylcyclotetrasiloxane, decamethylcyclopentasiloxane, dodecamethylcyclohexasiloxane, hexamethyldisiloxane, octamethyltrisiloxane, decamethyltetrasiloxane, dodecamethylpentasiloxane and mixtures thereof.

5. A preparation as set forth in claim 1, wherein the non-ionogenic W/O emulsifier is selected from the group consisting of sorbitan sesquioleate, sorbitan laurate, soya sterol, PEG-5 soya sterol, polyglyceryl-4 isostearate, polyglyceryl-2-PEG-4 isostearate, polyglyceryl-2 sesquiisostearate, cetyl-PEG/PPG dimethicone, trioleyl phosphate, trioleth-8, trilaureth-4-phosphate and mixtures thereof.

6. A preparation as set forth in claim 1, wherein the stabilisation agent is an inorganic salt which is soluble in water.

7. A preparation as set forth in claim 6, wherein the inorganic salt which is soluble in water is selected from the group consisting of sodium chloride, potassium chloride, sodium sulfate, magnesium sulfate and mixtures thereof.

8. A preparation as set forth in claim 7, wherein the inorganic salt is present in an amount of between 0.3 and 2% by weight, in the water phase.

9. A preparation as set forth in claim 1, wherein the moistening agent is selected from the group consisting of propylene glycol, dipropylene glycol, tripropylene glycol, butylene glycol, glycerine, diglycerine, triglycerine, sorbitol, mannitol, xylitol, glucose, fructose, sucrose, carbamide (urea), lactic acid, citric acid, pyrrolidone carboxylic acid (PCA) or the salts of said acids, preferably the sodium salts which are easily soluble in water, and mixtures of said substances.

10. A preparation as set forth in claim 1, wherein the moistening agent is present in the water phase in an amount of between 1 and 3% by weight.

11. A preparation as set forth in claim 1, wherein the preparation is suitable in the area of decorative cosmetics for caring for, coloring and improving skin, lips and eyelids.

12. A preparation as set forth in claim 1, wherein the preparation is selected from the group consisting of lip rouge, blusher, makeup, eyeshadow, camouflage and concealer.

13. A preparation as set forth in claim 1, wherein the preparation is an agent for fixing lipstick or lip rouge, a care foundation, a skin care agent or a sun protection agent.

14. A preparation as set forth in claim 1, wherein the preparation has a complex viscosity of between 800 and 6,000 Pas and a neutral viscosity of between 200,000 and 1,200,000 Pas.

15. A preparation as set forth in claim 1, wherein the preparation has a complex viscosity of between 800 and 6,000 Pas and a neutral viscosity of between 400,000 and 900,000 Pas.

16. A preparation as set forth in claim 14, wherein the neutral viscosity and complex viscosity were measured with a rheometer of type MCR-301 from Anton Paar (measuring system plate/plate, plates both sand-blasted, plate diameter 25 mm, gap width 1000 μm; software Rheoplus/32 V6.23).

17. A preparation as set forth in claim 1, wherein the wax has a dropping point of between 50 and 200° C.

18. A preparation as set forth in claim 1, wherein the wax has a dropping point of between 60 and 150° C.

19. A preparation as set forth in claim 1, wherein the wax has a dropping point of between 75 and 120° C.

20. A preparation as set forth in claim 1, wherein the wax has at least one alcohol residue with a chain length of between $C_2$ and $C_{60}$ and a carboxylic acid residue with a chain length of between $C_4$ and $C_{60}$.

21. A preparation as set forth in claim 20, wherein the wax has both at least one alcohol residue and also at least one carboxylic acid residue which has a saturated or singly or multiply unsaturated straight-chain or branched-chain hydrocarbon component.

* * * * *